United States Patent [19]

Kathawala et al.

[11] 4,448,785

[45] May 15, 1984

[54] N-UNSATURATED FATTY ACID AMIDES OF TRYPTOPHAN ESTER HOMOLOGUES AND ANTI-CHOLESTERIC USE THEREOF

[75] Inventors: Faizulla G. Kathawala, Mountain Lakes, N.J.; John G. Heider, West Nyack, N.Y.

[73] Assignee: Sandoz, Inc., E. Hanover, N.J.

[21] Appl. No.: 391,548

[22] Filed: Jun. 24, 1982

Related U.S. Application Data

[63] Continuation-in-part of Ser. No. 5,355, Jan. 22, 1979, abandoned, which is a continuation-in-part of Ser. No. 867,813, Jan. 9, 1978, abandoned.

[51] Int. Cl.$^3$ ............... C07D 209/20; A61K 31/405
[52] U.S. Cl. ............................. 424/274; 548/496
[58] Field of Search ............................. 548/496

[56] References Cited

FOREIGN PATENT DOCUMENTS 40-9134  5/1965  Japan .
40-10571 5/1965  Japan .

OTHER PUBLICATIONS

Suyama et al., "Chem Abst.", 66, Abst. 29058y (1967) of Yakugaku Zasshi 86(10) pp. 967–972 (1966).

*Primary Examiner*—Paul M. Coughlan, Jr.
*Assistant Examiner*—D. B. Springer
*Attorney, Agent, or Firm*—Gerald D. Sharkin; Richard E. Vila; Frederick H. Weinfeldt

[57] ABSTRACT

Ethylenically unsaturated fatty acid amides of tryptophan derivatives e.g. α-[1-oxo-9-octadecenylamino)]-1H-indole-3-propanoic acid, ethyl ester, are useful as pharmaceutical agents and are obtainable by reacting a mixed anhydride of a long chain unsaturated carboxylic acid with an appropriate tryptophan ester.

30 Claims, No Drawings

N-UNSATURATED FATTY ACID AMIDES OF TRYPTOPHAN ESTER HOMOLOGUES AND ANTI-CHOLESTERIC USE THEREOF

This is a continuation-in-part of copending application Ser. No. 5,355 filed Jan. 22, 1979, which in turn is a continuation-in-part of then copending application Ser. No. 867,813 filed Jan. 9, 1978 (both now abandoned).

This invention relates to organic compounds and more particularly to unsaturated fatty acid amides of tryptophan derivatives, and to pharmaceutical compositions containing such compounds, as well as to the pharmaceutical use of such compounds.

The compounds of this invention are conveniently represented by the formula I:

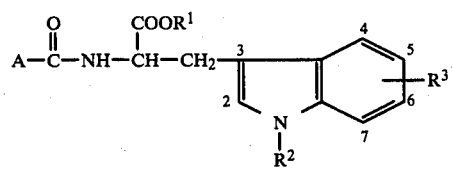

wherein
$R^1$ is alkyl having from 1 to 8 carbon atoms, preferably unbranched alkyl, and particularly ethyl; or benzyl;
$R^2$ is a hydrogen atom, alkyl having from 1 to 8 carbon atoms or benzyl;
$R^3$ is a hydrogen atom, halo having an atomic weight of from about 19 to 80, ie. fluoro chloro, or bromo, alkyl having from 1 to 3 carbon atoms, eg methyl, or alkoxy having from 1 to 3 carbon atoms, eg methoxy; and
A is the residue of an unsaturated long-chain fatty acid (minus the carboxylic portion).

It is preferred that when $R^3$ is other than a hydrogen atom, it be located at the 5-position of the indole nucleus. The moiety A is furnished by long-chain, unsaturated fatty acids having from 8 to 24 carbon atoms and having from 1 to 4 ethylenically unsaturated positions, which include, for example, oleic, linoleic, linolenic, arachidonic, palmitoleic, vaccenic, and parinaric acids. When $R^3$ is halo, it is one preferably having an atomic weight of from 19 to 36 ie fluoro or chloro.

Compounds I may be obtained by known acylation techniques (process a) of a DL-tryptophan derivative of formula II:

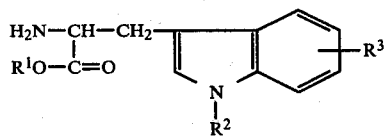

in which $R^1$, $R^2$ and $R^3$ are as defined above, with a long-chain, unsaturated fatty acid or derivative thereof corresponding to the moiety -A as defined above. Such "acylation" may be carried out by means conventionally employed in converting an amine function to its corresponding amide, such as are reported in the literature.

The acylation (process a) may conveniently be carried out by a mixed anhydride technique (process a1) wherein a compound II is treated with a mixed anhydride of the formula III:

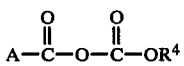

in which A is as defined above and $R^4$ is a lower unbranched alkyl having from 1 to 6 carbon atoms, at moderate temperatures, eg from about $-10°$ to $+35°$ C., in an inert organic medium, eg a chlorinated hydrocarbon, such as methylene chloride.

The mixed anhydrides (III) are obtainable by reacting (process b1) a free carboxylic acid of the formula IV:

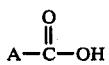

wherein A is as defined above, with a chloroformate of the formula V,

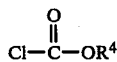

wherein $R^4$ is as defined above, in the presence of an acid acceptor, eg an organic base, such as triethylamine, at reduced temperatures, eg at from about $-10°$ to $+30°$ C., in an inert organic medium, eg a chlorinated hydrocarbon, such as methylene chloride.

A particularly convenient method of preparing compounds I comprises reacting (process a2) an acyl halide of the formula VI

in which A is as defined above, and X is either chloro or bromo, with a compound II (as defined above), in the presence of an acid acceptor, in an inert medium at moderate temperatures, eg from about 10° to 50° C. preferably at about 20° to 30° C.

The acyl halides (VI) may be prepared in the conventional manner, eg by treating (process b2) a corresponding compound IV (as defined above), with a halogenating agent capable of contributing a chlorine or bromine atom, eg thionyl chloride (or -bromide, as appropriate).

A particularly useful chlorinating agent is oxalyl chloride, as it yields acyl chlorides of high purity (compounds VI in which X=Cl), leading to final proudcts (I) of improved purity.

In the above-described processes, neither the media nor the temperature are critical to the reactions, and where the reactants or reagents are liquid, an excess thereof may serve as the reaction medium. If desired a compound II may be in the form of a watersoluble acid addition salt, for example the hydrochloride. The mixed anhydride (III) resulting from process (b1) may conveniently be used in situ. That is to say that provided that the materials in the reaction mixture containing the mixed anhydride are not detrimental, they may be used directly for process (a1) without recovery.

Embodiments of this invention are Compounds I in which A is of the formula:

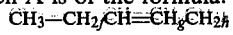 (A1)

 (A2)

wherein when A is (A1) then
 f = 1 to 10,
 g = 1 to 4, and
 h = 4 to 9 or 3 to 9;
particularly where f = 5 or 7, g = 1, and h = 7; and when A is (A2) then
 n = 1 to 4,
 m = 2 to 4, and
 p = 2 to 7 or 1 to 7;
particularly where
 n = 1 or 4, m = from 2 to 4 and p = 2 or 6.

The total number of carbon atoms in A1 or A2 conform to the definition of A, above. That is to say that since A is the residue of an acid having from 8 to 24 carbons; A has from 7 to 23 carbons and from 1 to 4 unsaturated positions. Radicals A which are unbranched are preferred. Also generally preferred are the fatty acid derivatives of the natural fatty acid order, ie those in which A represent an odd number of carbon atoms of from 7 to 23 and accordingly A–C=O represent an even number of carbon atoms of from 8 to 24.

Examples of acids suitable to provide A are given in tables I and II below:

TABLE I

| carbons in A—C=O | A = A1 | | | |
|---|---|---|---|---|
| | f | g | h | acid |
| 16 | 5 | 1 | 7 | palmitoleic |
| 18 | 7 | 1 | 7 | oleic |
| 18 | 10 | 1 | 4 | petroselenic |
| 18 | 5 | 1 | 9 | vaccenic |
| 18 | 3 | 3 | 7 | punicic (or eleostearic) |
| 18 | 1 | 4 | 7 | parinaric |
| 20 | 9 | 1 | 7 | gadoleic |
| 22 | 9 | 1 | 9 | cetoleic |

TABLE II

| carbons in A—C=O | A = A2 | | | |
|---|---|---|---|---|
| | n | m | p | acid |
| 18 | 4 | 2 | 6 | linoleic |
| 18 | 1 | 3 | 6 | linolenic |
| 20 | 4 | 4 | 2 | arachidonic |

Those compounds I wherein A is derived from oleic, linoleic, linolenic or arachidonic acids are particularly preferred.

It will be appreciated that the unsaturated acids which provide the moiety A occur in isomeric forms due to the presence of the one or more unsaturated positions. The particular isomeric form of the A moiety in a parent acid will remain the same in the resulting Compound I, since the structural configuration of the A moiety is not changed by the processes yielding compounds I. Compounds I wherein the hydrogen atoms on the pair of carbons of each unsaturated position of the A-moiety are in the cis configuration are preferred.

Particular embodiments of this invention are the compound α-[(1-oxo-9-octadecenylamino)]-1H-indole-3-propanoic acid, ethyl ester (cis isomer) as well as pharmaceutical compositions containing said compound as well as the use of said compound and compositions containing said compound as described herein.

Reagents and reactants described herein, e.g., compounds II, III, IV, V, and VI are known and obtainable by known means, or where not known, may be obtained by adaptation of methods reported in the literature for the preparation of known analogs; many such compounds being commercially available.

The final products and intermediate compounds described herein may be recovered and refined, where such is desired, by conventional means, such as by crystallization, distillation or chromatographic techniques such as column or thin layer chromatography.

STATEMENT OF UTILITY

The compounds of formula I of this invention are useful as pharmaceutical agents in animals. In particular, the compounds of the formula I are useful in controlling the cholesterol ester content of mammalian arterial walls and are therefore particularly indicated for use as anti-atherosclerotic agents, ie. agents useful in the prophylactic treatment of atherosclerosis and in the controlling of atherosclerotic conditions due to cholesterol ester accumulation in the arterial walls. Such ability of the compounds of the formula I is indicated e.g., by known test procedures in which the total cholesterol ester content of cultured cells is shown to be reduced by a test compound, as compared to untreated cells, and carried out, for example, by the following procedures:

(A) Cell Culture

Rhesus monkey smooth muscle cells (from the arterial, eg aorta wall) obtained by the method of K. Fisher-Dzoga et al (Experimental and Molecular Pathology 18, 162–176 (1973)) are routinely grown in 75 $cm^2$ tissue culture flasks using Minimum Essential Medium (Eagle) supplemented with 10% fetal bovine serum. For testing a 75 $cm^2$ flask with a near confluent cell growth is selected. The cells are removed from the flask surface by mild enzymatic treatment with pronase. After centrifugation and decanting the enzyme solution, the cell pellet is resuspended in an appropriate volume of media for seeding the desired number of 60 mm tissue culture dishes. Five (5) ml of the diluted cell suspension are pipetted into each dish. After seeding, the dishes are labelled with the cell type, date and flask number of origin and incubated at 37° C. in approximately 5% $CO_2$ atmosphere in a high humidity incubator. When the cultures are confluent, the actual drug testing is begun. Test compounds are routinely solubilized in 100% ethanol. An equivalent amount of ethanol is added to control groups as well. The tissue culture dishes are randomly divided into groups. To one group, hyperlipemic rabbit serum (HRS) is added at 5% by volume (control). To the remaining groups, 5% HRS and 1 mg per 100 ml of media of the test compound are added. The dishes are returned to the incubator for an additional 24 hours. All operations through to the final incubation are performed using sterile technique in a laminar flow hood. After the incubation period, the dishes are microscopically observed with the Zeiss Axiomat with phase contrast optics and the conditions of the cultures are recorded; especially in regard to the size, number and configuration of cytoplasmic inclusions and to cellular morphology. The media is removed from the cultures and 0.9% sodium chloride solution is added. The cells are removed from the flasks with the aid of a rubber policeman and transferred to a conical graduated centrifuge tube. The cells are washed three times by suspending in an isotonic salt solution, centrifuging at 800× g for 10 minutes and aspirating the supernatant fluid.

(B) Cell extraction procedure

An appropriate volume of isopropyl alcohol (about 1 ml/mg protein) is then added to the cell pellet and the sample sonicated with a micro probe (140×3 mm) for 10 seconds with a "LO" setting of 50 on a Bronwell Biosonik IV. After centrifugation for 15 minutes at 800× g, the clear supernatant is decanted and an aliquot taken for cholesterol analysis.

The residue is dissolved in 0.1 N sodium hydroxide and an aliquot taken for protein determination by the method of Lowry, et al. (J. Biol. Chem. 193, 265; 1951).

(C) Assay

Free cholesterol: The isopropyl alcoholic solutions of standards, samples and blank (isopropyl alcohol alone) are treated in a similar manner. An aliquot of 0.4 ml of free reagent (Reagent A, Table 1 below) is added to a 10×75 mm disposable glass test tube to which 20 μl of the isopropyl alcoholic solution is added and mixed. After standing at room temperature for approximately 5 minutes, 0.8 ml of 0.5 N sodium hydroxide (Reagent C, Table 1) is added and mixed. The fluorescence is measured with an Aminco-Bowman spectrophotofluorometer with an excitation wavelength of 325 nm and emission wavelength of 415 nm. A 1 cm light path cuvette is used with a xenon lamp, an IP28 photomultiplier tube and 2 mm slits.

Total cholesterol: The same procedure described above for free cholesterol is followed for total cholesterol except that the total reagent (Reagent B, Table 1) is used instead of the free reagent and the samples are incubated for 20 minutes at 37° C. before the addition of the 0.5 N sodium hydroxide solution (Reagent C, Table 1).

Alternatively the assay for cholesterol, ie Step C (above) obtained from Steps A and B, may be carried out by the method of Ishikawa et al (J. Lipid Res. 15, 286; 1974).

The amount of cholesterol ester is found by subtracting the amount of free cholesterol from the total cholesterol content of the cells determined by the assay. A finding of a lower amount of cholesterol ester in the group of cells to which test compound was added, as compared to the control group (untreated) shows that the test compound is active in reducing the cholesterol ester in the cells.

TABLE 1

Composition of Reagents for Cholesterol Determination

| | | |
|---|---|---|
| A. Free Cholesterol Reagent | | |
| Sodium phosphate buffer pH 7.0 | .05 | M |
| Cholesterol oxidase | .08 | U/ml |
| Horseradish peroxidase | 30. | U/ml |
| p-Hydroxyphenylacetic acid | .15 | mg/ml |
| B. Total Cholesterol Reagent | | |
| Sodium phosphate buffer pH 7.0 | .05 | M |
| Cholesterol esterhydrolase | .08 | U/ml |
| Cholesterol oxidase | .08 | U/ml |
| Horseradish peroxidase | 30. | U/ml |
| Sodium taurocholate | 5. | mM |
| Carbowax-6000 | .17 | mM |
| p-Hydroxphenylacetic acid | .15 | mg/ml |
| C. Sodium Hydroxide Solution | .5N | |

Comparative test results are reported in Table 2 below, in which monkey aortic smooth muscle cells were originally obtained from Dr. K. Fisher-Dzoga: Univ. of Chicago, the test compound (Compound A) is α-[(1-oxo-9-octadecenylamino)]-1H-indole-3propanoic acid (cis-form); (product of Example 2)

TABLE 2

Comparative Test

| Compound | Protein mg/ culture | Cholesterol (μg/mg cell protein) | | | | Percent from control |
|---|---|---|---|---|---|---|
| | | Total | Free | Ester Amount | Ester mean | |
| None (Control) | 0.272 | 73.1 | 50.0 | 23.1 | 22.3 | — |
| None | 0.324 | 65.1 | 43.7 | 21.4 | | |
| A | 0.284 | 57.4 | 50.4 | 7.0 | 6.5 | 71.0* ↓ |
| A | 0.310 | 60.3 | 54.4 | 5.9 | | |

*significant at P less than 0.01

The compounds of the formula I as represented by the compound of Example 2a hereinafter, are also useful as general agents for the lowering of serum cholesterol and cholesterol ester levels e.g., as anti-atherosclerotic agents, as indicated by oral administration at a dose of 200 mg/kg of the test compound per day for 9 weeks to rabbits in conjunction with a high cholesterol diet resulting in, compared to controls, a reduction in cholesterol and cholesterol ester serum levels, as well as lessened formation or absence of arterial wall plaques.

The activity of Compounds I for the advantageous control of cholesterol levels in a host, is also indicated by the Zilversmit test, which indicates whether a compound inhibits the absorbtion of exogenous cholesterol (free and/or ester form) by action at the intestinal wall (gut) of a host. The Zilversmit test is carried out as follows:

(a) Purification of the Isotopes

Cholesterol-1-2-$^3$H and cholesterol-4-$^{14}$C were obtained from New England Nuclear. They were purified by high pressure liquid chromatography (Beckman Model 332) using a reverse phase ultrasphere O.D.S. 25 cm×4.5 mm I.D. column with the following solvent system:

Solution A-60% acetonitrile, 40% Isopropyl alcohol
Solution B-40% acetonitrile, 40% Isopropyl alcohol, 20% heptane
(All reagents Baker HPLC grade)

The flow rate was 1 ml/min. Detection was made at 206 nm using a Model 155-40 UV-Vis detector (Beckman). The radioactive cholesterol solution in benzene was evaporated to dryness, taken up in isopropyl alcohol and injected into the HPLC in five 20 μl aliquots. Cholesterol fractions were collected, pooled and evaporated to dryness. The purified fraction was rechromatographed under the same conditions to confirm purity.

(b) Preparation of Isotopic Cholesterol Doses

(b1) Intravenous

The HPLC-purified cholesterol-1-2-$^3$H was dissolved in corn oil (M.C.B.U.S.P.). The corn oil solution was added to 6.8% skim milk in a ratio of 1:4. This mixture was homogenized by sonicating with a Bronwell Biosonik IV sonicator using a microprobe at a "Lo" setting of 50 until a homogenous suspension was formed. One rabbit was selected from a group which has been on 1% cholesterol diet about 10 weeks. The rabbit was given the entire $^3$H dose (2900 μCi/71.2 n moles) by gavage. Eighteen hours later the rabbit was exsanguinated and serum obtained. This was sterilized by running through a Millipore Sterifil-D-GS 0.22 μm filter unit. Each rabbit in the study received 1.5 ml of this serum containing 3.0 μCi/0.7 n moles cholesterol-1-2-$^3$H.

(b2) Oral

Cholesterol-1-4-$^{14}$C was dissolved in corn oil (M.C.B.U.S.P.). The corn oil solution was added to 6.8% skim milk in a ratio of 1:4. The resulting mixture was homogenized by sonicating with a Bronwell Biosonik IV sonicator using a microprobe at a 37 Lo" setting of 50 until a homogenous suspension was formed. Each animal received 1 ml of this preparation by gavage containing 0.5 μCi/8.42 n moles cholesterol-4-$^{14}$C. Aliquots were taken for assay at the start, midpoint and end of the oral isotope administration.

(c) Administration of Drug Dose

Doses of test compound A, B, C and D were administered by gavage as a suspension in carboxymethyl cellulose (1.5% CMC solution in water). The Control group received an equal volume of CMC solution. The drugs were administered for three days. On the third day the drug was given 16 minutes before oral isotope and 18 minutes before i.v. isotope adminstration.

(d) Animals

Male New Zealand rabbits were divided into approximately equal groups by weight and serum cholesterol levels. Rabbit chow with 2.1% cholesterol (BioServ Inc.) and water were given ad libitum for one week before drug dosing and throughout the study except for an overnight fast before isotope dosing and until four hours after the isotope dosing.

(e) Sample Collection

Blood samples were taken by cardiac puncture at 72 hours. Duplicate 0.2 ml aliquots of serum were placed on combustion papers and dried before combustion in the packard 306 Tri-Carb Sample Oxidizer.

(f) Radioactive Analysis

The radioactivity was determined by liquid scintillation counting in either a Packard 3320 Liquid Scintillation Spectrometer or a Beckman Model LS8000. The scintillation fluids for $^{14}$C were Carbosorb II and Permafluor V. Monophase was used for $^3$H. Permafluor was used for direct counting of the dose assays.

(g) Calculations

The combined efficiency of the oxidizer and liquid scintillation counter was determined for each isotope from standards of known specific activity.

$$\text{Eff.} = \frac{\text{cpm Std.}}{\text{dpm Std.}}$$

Samples were converted to dpm after blank subtraction $$\text{dpm sample} = \frac{\text{cpm sample}}{\text{Eff.}}$$

$$\text{Absorption (\%)} = \frac{\frac{^{14}C \text{ sample } dpm}{^{14}C \text{ oral dose } dpm}}{\frac{^3H \text{ sample } dpm}{^3H \text{ i.v. dose } dpm}} \times 100$$

Tests were run on the compound 2a by the Zilversmit method, and are reported, below, in Tables 3 and 4:

TABLE 3

EFFECT ON CHOLESTEROL ABSORPTION IN THE CHOLESTEROL FED RABBIT

| Treatment (Dose) | Percent Cholesterol Absorption[a] | n | % change |
|---|---|---|---|
| Control | 41.0 ± 3.3 | 9 | — |
| Test Compound* | 11.2 ± 1.1 | 4 | ↓72.6%[b] |

[a]Mean ± S.E.M.
[b]Significant at P 0.001
n = number of animals
*compound of Example 2a at 500 mg/kg.

TABLE 4

| Treatment (Dose) | Percent Cholesterol Absorption[a] | n | % change |
|---|---|---|---|
| Control | 43.0 ± 2.03 | 3 | — |
| Test Compound* | 20.0 ± 1.43 | 4 | ↓53.5[b] |

[a]± S.E.M.
[b]Significant at P < 0.001
*Compound of Example 2a at 200 mg/kg.

The above described cell culture test may alternatively be carried out using as the cells Fu5AH rat hepatoma cells (Rothblat, G. M., Lipids 9, 526–535; 1974). Tests of the compound of Example 2a again show marked inhibition of cholesterol accumulation by cells (as in Table 2 above). Also, other representative compounds I showed positive activity (all by visual observation) and in two cases the procedure was carried out to obtain numerical data; reported in Tables 5 and 6 below.

TABLE 5

Inhibition of Cholesterol Ester Accumulation in Fu5AH Cells

| Treatment | Dose μg/ml | Protein[a] mg/culture | Cholesterol[a] μg/mg Cell Protein | | | % inh[f] |
|---|---|---|---|---|---|---|
| | | | Total | Free | Ester | |
| Normal Control[b] | — | 0.09 ± 0.03 | 25.1 ± 3.1 | 13.7 ± 2.0 | 11.4 ± 1.1 | |
| Hyperlipemic Control[c] | — | 1.10 ± 0.06 | 193.0 ± 2.9 | 40.7 ± 0.6 | 152.5 ± 2.3 | |
| Compound of Example 2a | 10 | 0.71 ± 0.03[e] | 117.4 ± 5.2[e] | 76.8 ± 6.5[e] | 40.6 ± 1.3[e] | 73 |

[a]Mean ± SEM
[b]Normal cells grown in EMEM-10% FBS (n = 3)
[c]5% HRS + 1% DMSO (n = 3)
[d]5% HRS + Test Compound in DMSO (n = 3)
[e]Significant from Hyperlipemic Control at p < .01
[f]% inh = % inhibition = $\frac{\text{Hyperlipemic Control (ester)} - \text{Test (ester)}}{\text{Hyperlipemic Control (ester)}} \times 100$

TABLE 6
INHIBITION OF CHOLESTEROL ESTER ACCUMULATION IN Fu5AH CELLS IN COMPOUNDS I

| Compound of Example | Dose mg/ml | Visual[a] | F/T[b] | % Inhibition[c] |
|---|---|---|---|---|
| 1 | 10 | About same | — | 69%, 59% |
| 3a | 10 | About same | 0.52 (Control = 0.17) | — |
| 3b | 10 | About same | 0.45 (Control = 0.17) | — |
| 3e | 10 | About same | — | 39% |
| 4c | 5 | Weaker | 0.22 (Control = 0.19) | — |
| 4d | 10 | About same | — | — |

[a]visual observations* are in comparison to results with compound of Example 2a.

[b]F/T = $\frac{\text{Free cholesterol}}{\text{Total cholesterol}}$

Note:
the F/T for compound of Example 2a, calculated from Table 5 is 0.65, (hyperlipemic control = 0.21).

[c]% inhib. = % inhibition of cholesterol ester accumulation.

*At the point in Step A of the cell culture test where cultures are observed regarding the condition of the cells (cytotoxicity) and any alterations in the shape, size or number of lipid inclusions relative to the control and standard, a qualitative assessment of inclusions in test compound treated group relative to control and standard is made, re, (1) no drug effect; (2) reduced number of inclusions <, =, > standard.

The antiatherosclerotic effective dosage of active ingredient employed for the reduction of cholesterol ester content in the arterial walls of a mammal may vary depending on the particular compound employed, the mode of administration and the severity of the condition being treated. However, in general, satisfactory results are obtained when the compounds of formula I are administered at a daily dosage of from about 2 milligrams to about 500 milligrams per kilogram of animal body weight, preferably given in divided doses two to four times a day, or in sustained release form. For most large mammals, the total daily dosage is from about 100 mg. to about 15,000 mg., preferably from about 100 mg. to 5,000 mg., eg. 300 mg. to 5000 mg. Dosage forms suitable for internal use comprise from about 25 to 7,500 mg. e.g., 25 to 2,500 mg. of the active compound in intimate admixture with a solid or liquid pharmaceutically acceptable carrier. Solid carriers include starch, lactose and kaolin, while liquid carriers include sterile water, polyethylene glycols and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants eg vitamin E, ascorbic acid, BHT and BHA.

The compounds are preferably administered orally. The preferred pharmaceutical compositions from the standpoint of ease of preparation and administration are solid compositions for oral administration, particularly tablets and hard-filled or liquid-filled capsules.

Where the final product (I) is waxy or oily and oral dosages in the higher ranges are desired, the product may conveniently be administered in an aqueous suspension; the flavor thereof being enhanced by fruit flavors and the like, e.g., as a "milk shake" or "cocktail", by methods well known in the art, e.g., using CMC as a suspending agent.

When the compounds I are employed for the above utility, they may be combined with one or more pharmaceutically acceptable carriers, e.g., solvents, diluents and the like, and may be administered orally in such forms as tablets, capsules, dispersible powders, granules, suspensions containing, for example, from about 0.5 to 5% of suspending agent, syrups containing, for example, from about 10 to 50% of sugar, and elixirs containing, for example, from about 20 to 50% ethanol, and the like, or parenterally in the form of sterile injectable solutions of suspensions containing from about 0.5 to 5% suspending agent in an isotonic medium. These pharmaceutical preparations may contain, for example, from about 0.5% up to about 90% of the active ingredient in combination with the carrier, more usually between 5% and 60% by weight.

A representative formulation for administration orally three times a day prior to feeding in the treatment of atherosclerosis is a gelatin caspule prepared by conventional techniques to contain the following

| Ingredient | Weight (in Mg.) | | |
|---|---|---|---|
| α-[(1-oxo-9-octadecenylamino)]-1H—indole-3-propanoic acid, ethyl ester (cis form) | 300 | 300 | 500 |
| corn oil | 500 | 200 | — |

As is the present understanding in the art, controlling the total cholesterol content of an arterial wall by inhibiting the accumulation thereof by reducing the cholesterol ester content thereof, advantageously inhibits the formation of plaques in the arterial wall.

The above evaluations indicate that the compounds of the formula I effect their anti-arthersclerotic activity predominately if not essentially exclusively by the desirable mode of action of blocking the absorption of cholesterol in the gastro-intestinal tract and it is further indicated accordingly that very little at most of these active ingredients are absorbed into the systemic system. Additional assay investigations also indicate that such blocking is due largely or essentially solely to action of the compounds on the ACAT enzyme but we do not intend to be limited to any theory by which such blocking action is effected.

The following examples are illustrative of the invention. All temperatures are centigrade and room temperature is 20° to 30° C.; unless indicated otherwise. Reduced pressures are in mm of mercury.

Where NMR characterization data is presented, the analysis is run in $CDCl_3$ and values given in ppm; digits in parenthesis are number of protons; and t=triplet, d=doublet and s=singlet.

EXAMPLE 1

α-[(1-Oxo-9,12-oxtadecadienylamino)]1H-Indole-3-Propanoic acid, Ethyl Ester(cis, cis isomer)

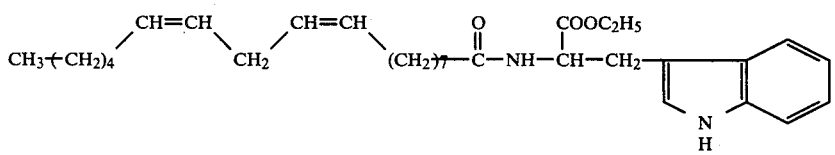

To a solution of 7.0 g linoleic acid in 150 ml methylene chloride cooled to −20° is added 2.5 g. triethylamine and then 2.7 g. ethyl chloroformate. The reaction mixture is stirred for two hours and gradually allowed to warm to room temperature. There is then added 2.5 g triethylamine followed by 6.7 g. of DL tryptophan ethyl ester hydrochloride and the reaction mixture is stirred for 18 hours. The reaction mixture is then extracted several times with 2 N aqueous sodium hydroxide washed with saturated aq. sodium chloride solution, and the organic phase dried over anh. sodium sulfate, filtered and the filtrate evaporated i.v. to dryness. The residue is then filtered over silica gel using chloroform as the eluant to obtain the title product in solvent, which is then evaporated to yield the title product as a waxy solid; NMR: t 5.4 (4), d 6.1 (1), s 8.8 (1).

EXAMPLE 2

Repeating the procedure of Example 1, but using in place of the linoleic acid used therein, an approximately equivalent amount of:
(a) oleic acid;
(b) linolenic acid;
(c) palmitoleic acid; or
(d) arachidonic acid;
there is accordingly obtained:
(a) α-[(1-oxo-9-octadecenylamino)]-1H-indole-3-propanoic acid, ethyl ester (cis isomer) (waxy solid); NMR: t 5.3 (2), d 6.2 (1), s 9.2 (1);
(b) α-[(1-oxo-9,12,15-octadecatrienylamino)]-1H-indole-3-propanoic acid, ethyl ester (cis, cis cis isomer);
(c) α-[(1-oxo-9-hexadecenylamino)]-1H-indole-3-propanoic acid, ethyl ester (cis isomer); and
(d) α-[(1-oxo-5,8,11,14-eicosatetraenylamino)]-1H-indole-3-propanoic acid, ethyl ester (cis,cis,cis,cis isomer).

EXAMPLE 3

Repeating the procedure of Example 2a, but using in place of the tryptophan ethyl ester hydrochloride used therein, an approximately equivalent amount of either the free amino form or hydrochloride of:
(a) 2-amino-3-(1- methylindolyl)-propanoic acid, ethyl ester;
(b) 2-amino-3-(1H-5-methoxyindolyl)-propanoic acid, ethyl ester;
(c) 2-amino-3-(1H-5-chloroindolyl)-propanoic acid, ethyl ester;
(d) 2-amino-3-(1-benzylindolyl)-propanoic acid, ethyl ester; or
(e) 2-amino-3-(1H-5-fluoroindolyl)-propanoic acid, ethyl ester;
There is accordingly obtained (as cis isomers):
(a) 2-(1-oxo-9-octadecenylamino)-3-(1-methylindolyl)-propanoic acid, ethyl ester; (oil) NMR: t 5.35 (2), d 6.0 (1), s 3.7 (3);
(b) 2-(1-oxo-9-octadecenylamino)-3-(1H-5-methoxyindolyl)-propanoic acid, ethyl ester; (wax) NMR: t 5.4 (2), d 6.1 (1), s 8.4 (1) and s 4.85 (3);
(c) 2-(1-oxo-9-octadecenylamino)-3-(1H-5-chloroindolyl)-propanoic acid, ethyl ester;
(d) 2-(1-oxo-9-octadecenylamino)-3-(1-benzylindolyl)-propanoic acid, ethyl ester; and
(e) 2-(1-oxo-9-octadecenylamino)-3-(1H-5 fluoroindolyl)-propanoic acid, ethyl ester; (wax) NMR: t 5.3 (2), d 6.1 (1), s 8.7 (1).

EXAMPLE 4

Repeating the procedure of Example 1 but using in place of the ethyl ester of tryptophan hydrochloride (as compound II) used therein, an approximately equivalent amount, as the $R^1$ contributing reactant, the analogous: (a) n-propyl; (b) n-butyl; (c) n-octyl; or (d) benzyl ester; the corresponding: (a) n-propyl; (b) n-butyl; (c) n-octyl*; and (d) benzyl ester** analogs of the title products of Example 1 are obtained.
*mp 66–68°;
**(oil)NMR: t 5.35 (4), d 6.1 (1), s 8.5 (1) and s 5.1 (2).

EXAMPLE 5

Repeating the procedure of Example 2a, but using in place of the ethyl ester of tryptophan hydrochloride (as compound II) used therein, an approximately equivalent amount, as the $R^1$ contributing reactant, the analogous: (a) n-propyl; (b) n-butyl; (c) n-octyl; or (d) benzyl ester; the corresponding: (a) n-propyl; (b) n-butyl; (c) n-octyl; and (d) benzyl ester anologs of the product of Example 2a are obtained.

EXAMPLE 6

α-[(1-Oxo-9-octadecenylamino)]-1H-Indole-3-Propanoic Acid, Ethyl ester (cis)

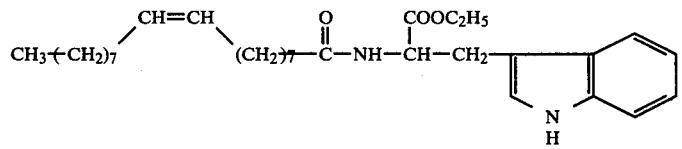

To a solution of 10.5 g oleic acid in 200 ml of methylene chloride, cooled to −20° is added 3.7 g triethylamine and then 4.0 g chloroethylformate. The solution is allowed to come to room temperature gradually and then stirred 2 hrs. at r.t.

Thereafter 3.7 g triethylamine is added, followed by 9.9 g (DL) tryptophane ethyl ester hydrochloride, and the reaction mixture is stirred 16 hours at r.t.

The reaction mixture is then washed first with 2 N hydrochloric acid followed by brine, then 2 N sodium hydroxide, followed by brine. The organic phase is then dried over anh. sodium sulfate, filtered and evaporated i.v. to give a clear oil. On tituration with pentane, a waxy solid is obtained. The waxy solid is then filtered over silica gel with chloroform as eluant to give refined title product.

EXAMPLE 7

α-[(1Oxo-9-octadecenylamino)]-1H-Indole-3-Propanioc Acid, Ethyl ester (cis)

Step A. Oleyl Chloride

Into a dry 4-neck-round bottomed flask equipped with nitrogen inlet, addition funnel, therometer, mechanical stirrer and heating means, under nitrogen, are cautiously (to avoid foaming), charged 229 g. of oleic acid (99% pure, m.p. 4°; b.p. 286°/100 mmHg), 263 ml of toluene and 109 ml. of oxalyl chloride (b.p. 63°–64°), at a rate so as to keep the (internal) reaction temperature between 25°–30°, over a period of about 15 minutes. After addition is complete the funnel is washed with an additional 25 ml. toluene. The reaction mixture is stirred 25°–30° for about one-half hour, and then at about 50°–55° for 1 hour. The toluene is then distilled off (initially at 35°–40°/63 mm vapor pressure; then at 30°–25°/26 mm for 1.5 hours) to obtain oleyl chloride, which is promptly used for the following Step B.

Step B

In apparatus similar to that of Step A, but larger, is added, under nitrogen, 192.2 g. of D,L-tryptophan ethyl ester hydrochloride, 2.57 liters of dry toluene, and 248 ml. of triethylamine. The mixture is stirred until homogenous and a solution of 215 g. of oleyl chloride (from Step A) in 475 ml. of dry toluene is added, dropwise, at such a rate to keep the reaction mixture at an (internal) temperature of between 25°–30° (about 70 minutes). The funnel is washed with 50 ml. of toluene and the mixture stirred for an hour after addition is complete (reaction completion can be determined by TLC observing ratio of starting materials to product).

The reaction mixture is transferred to a separatory funnel and the reaction vessel rinsed with 100 ml. toluene, and the combined organic phases are washed with 1.43 liters of 2 N hydrochloric acid, the organic phase retained and washed with a solution composed of:
133 g. of 50% aq. sodium hydroxide,
529 g. of 30% aq. sodium chloride, and
166 g. of water.
The organic phase is then washed with a solution of:
570 g. of 30% aqueous sodium chloride, in
285 g. of water.

The organic phase is then concentrated, under vacuum, at 60° to obtain crude product as a light oil. The oil is taken up in 1.396 liters of absolute alcohol, the resulting alcoholic mixture is filtered and then cooled to −5°. 150 ml. of water is then added dropwise, to the alcoholic mixture, over a period of about 15 minutes, and then 500 ml. of water is then added at from 0° to 3° over a period of 25 minutes. Further water (745 ml) is added at 5° over 5 minutes and stirred for one-half hour. The resulting precipitates are recovered by filtration (using a Buchner funnel and filter paper). The filtrate is used to wash any remaining solids on to the filter. The solids are washed on the filter with 2 liters of water, then dried at 65°/50 mm for 12 hours, highly-refined title product as a white solid, m.p. 78.5° to 79.5°.

What is claimed is:

1. A compound of the formula

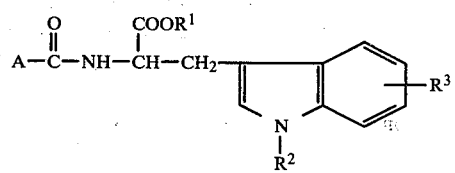

wherein
$R^1$ is alkyl having from 1 to 8 carbon atoms or benzyl
$R^2$ is a hydrogen atom, alkyl having from 1 to 3 carbon atoms or benzyl;
$R^3$ is a hydrogen atom, halo having an atomic weight of from about 19 to 80, alkyl having from 1 to 3 carbon atoms, or alkoxy having from 1 to 3 carbon atoms;
A is the residue of an unsaturated long-chain fatty acid minus the carboxylic portion, said acid having from 8 to 24 carbon atoms and having from 1 to 4 ethylenically unsaturated positions.

2. A compound of claim 1 in which A is of either the types (A1) having the structure:

$$CH_3-(CH_2)_f-(CH=CH)_g-(CH_2)_h;\text{ or}$$

(A2) having the structure $$CH_3-(CH_2)_n-(CH=CH-CH_2)_m(CH_2)_p$$

in which f is a whole integer of from 1 to 10, g is a whole integer of from 1 to 4, and h is a whole integer of from 4 to 9;
n is a whole integer of from 1 to 4,
m is a whole integer of from 2 to 4,
and p is a whole integer of from 2 to 7.

3. A compound of claim 2 in which A is of type (A1).

4. A compound of claim 3 in which A is the residue of oleic acid.

5. A compound of claim 3 in which A is the residue of palmitoleic acid.

6. A compound of claim 2 in which A is of type (A2).

7. A compound of claim 6 in which A is the residue of linoleic acid.

8. A compound of claim 6 in which A is the residue of linolenic acid.

9. A compound of claim 1 in which $R^2$ is a hydrogen atom.

10. A compound of claim 1 in which $R^3$ is a hydrogen atom.

11. A compound of claim 1 in which $R^1$ is ethyl.

12. The compound of claim 1 which is α-[(1-oxo-9,12-octadecadienylamino)]-1H-indole-3-propanoic acid, ethyl ester (cis, cis isomer).

13. The compound of claim 1 which is α-[(1-oxo-9octadecenylamino)]-1H-indole-3-propanoic acid, ethyl ester (cis isomer).

14. A method of controlling the cholesterol ester content of an arterial wall, in a mammal in need of such treatment, comprising orally administering a cholesterol ester-controlling amount of a compound of claim 1 to said mammal.

15. A pharmaceutical composition suitable for controlling the cholesterol ester content of an arterial wall of a mammal comprising a cholesterol ester-controlling effective amount of a compound of claim 1 and a non-toxic pharmaceutically-acceptable carrier.

16. A composition of claim 15 in solid form.

17. A composition of claim 15, in which the compound is present in an amount of from about 25 to 2,500 milligrams.

18. A composition of claim 16 in which the compound is α-[(1-oxo-9-octadecenylamino)]-1H-indole-3-propanoic acid, ethyl ester (cis isomer).

19. The compound of claim 1 which is α-[(1-oxo-9,12-octadecadienylamino)]-1H-indole-3-propanoic acid, n-octyl ester (cis,cis isomer).

20. The compound of claim 1 which is α-[(1-oxo-9,12-octadecadienylamino)]-1H-indole-3-propanoic acid, benzyl ester (cis,cis isomer).

21. A compound of claim 1 in which each unsaturated position of A is in the cis-type isomeric form.

22. The compound of claim 1 which is 2-(1oxo-9-octadecenylamino)-3-(1-methylindolyl)-propanoic acid, ethyl ester (cis isomer).

23. The compound of claim 1 which is 2-(1oxo-9-octadecenylamino)-3-(1H-5-methoxyindolyl)-propanoic acid, ethyl ester (cis isomer).

24. A method of claim 14 in which the compound is administered at a daily dosage of from about 100 milligrams to about 5,000 milligrams.

25. A method of claim 14 in which the compound is administered at a daily dosage of from about 100 milligrams to about 15,000 milligrams.

26. A method of claim 14 in which the compound is α-[(1oxo-9-octadecenylamino]1H-indole-3-propanoic acid, ethyl ester (cis isomer).

27. A compound of claim 1 in which $R^3$ is fluoro or chloro.

28. A compound of claim 1 in which $R^1$ is unbranched.

29. A compound of claim 1 in which A has an odd number of carbon atoms.

30. A compound of claim 1 in which $R^1$ is ethyl.

* * * * *